United States Patent

Hill et al.

[11] Patent Number: 6,013,683
[45] Date of Patent: Jan. 11, 2000

[54] SINGLE PHASE SILICONE AND WATER COMPOSITIONS

[75] Inventors: Randal Myron Hill, Midland, Mich.; Eric William Kaler, Newark, Del.; Larry Daniel Ryan, Waterford, N.Y.; James Alexander Silas, Newark, Del.

[73] Assignees: Dow Corning Corporation, Midland, Mich.; University of Delaware, Newark, Del.

[21] Appl. No.: 09/213,512

[22] Filed: Dec. 17, 1998

[51] Int. Cl.⁷ .............................. B01J 13/00; A61K 7/06
[52] U.S. Cl. .................... 516/67; 424/70.12; 424/70.19; 424/70.28; 514/846; 514/938; 516/76
[58] Field of Search .................... 516/67, 76; 424/70.12, 424/70.19, 70.28; 514/938, 846

[56] References Cited

U.S. PATENT DOCUMENTS

| | | | |
|---|---|---|---|
| 4,726,945 | 2/1988 | Patel et al. | 424/70.12 |
| 4,778,624 | 10/1988 | Ohashi et al. | 516/67 |
| 5,152,924 | 10/1992 | Gee | 516/67 X |
| 5,162,378 | 11/1992 | Guthauser | 514/938 X |
| 5,298,240 | 3/1994 | Schröder et al. | 424/70.19 |
| 5,520,827 | 5/1996 | Danner | 516/67 X |
| 5,556,629 | 9/1996 | Traver et al. | 516/76 X |
| 5,563,189 | 10/1996 | Hosokawa et al. | 516/76 X |
| 5,705,562 | 1/1998 | Hill | 524/731 |

*Primary Examiner*—Richard D. Lovering
*Attorney, Agent, or Firm*—James L. Cesare

[57] ABSTRACT

A clear single phase composition contains 40–95% by weight of a cyclic or short chain linear methyl siloxane and water, and 5–60% by weight of a cationic surfactant and a nonionic surfactant. The cyclic or short chain linear methyl siloxane in the single phase composition has an average structure or droplet diameter of less than about 50 nanometer. The single phase composition spontaneously provides optically clear one phase silicone microemulsions when combined with only hand agitation. The clear single phase compositions are useful in personal care and textile applications.

2 Claims, No Drawings

SINGLE PHASE SILICONE AND WATER COMPOSITIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a composition in the form of a single phase that contains a silicone and water. More particularly, the composition is a single or one phase transparent, thermodynamically stable, mixture of two or more immiscible liquids, i.e., silicone and water, and a surfactant(s). The composition is stable at temperatures generally in the range of about 15–75° C.

BACKGROUND OF THE INVENTION

This invention is directed to an optically clear single phase silicone microemulsion formed with very little input of mechanical energy for mixing the components. More particularly, a ternary composition of water, a cyclic or short chain linear methyl siloxane, and a nonionic surfactant or a combination of a nonionic surfactant and a cationic surfactant, spontaneously provides optically clear one phase silicone microemulsions, when combined and gently mixed by handshaking or stirred with a magnetic stirrer.

It is well documented (U.S. Pat. No. 4,999,398) that emulsions, especially silicone emulsions, are opaque, cloudy, and tend to separate on standing. Microemulsions, in contrast, are desirable because they are thermodynamically stable and contain equilibrium microstructures that are smaller than typical emulsion droplets. Thus, the products are indefinitely stable and can be optically clear.

As used herein, the term emulsion or macroemulsion means a mixture of one immiscible liquid in another, in the form of droplets, with diameters approximately in the range of 100–1,000 nanometer (0.1–1.0 micron/1,000–10,000 angstrom Å). In contrast, a microemulsion means a single or one phase transparent, thermodynamically stable, mixture of two or more immiscible liquids and one or more surfactants and co-surfactants.

In order to avoid confusion, it should be noted that the term microemulsion has been used in the literature to describe any transparent composition containing water, oil and a surfactant, including compositions which are transparent by virtue of a very small structure size and index of refraction matching. However, it is almost always apparent from the details of the preparation given which type of composition is in fact being made, considering the order of addition of the components, their polymerization, or when high energy mixing is involved.

Microemulsions are clear or transparent because they contain structures smaller than the wavelength of visible light, which is typically on order of about 500 nanometer. Furthermore, microemulsions, as that term is being used herein, contain structures that are spontaneously self-assembled aggregates consisting of oil and surfactant monolayers, or water and surfactant monolayers. Although there are distinct domains present which are composed of water and oil, the system is properly described as one phase, because the domains consist of molecular aggregates that spontaneously self-assemble.

Microemulsions may contain oil droplets dispersed in water (O/W), water droplets dispersed in oil (W/O), or they may be in the form of a bicontinuous structure or other structure. They are characterized by an ultra-low interfacial tension between the microemulsion and any excess oil-rich or water-rich phase.

A microemulsion can be recognized by several of its inherent characteristics which are that (i) it contains oil, water, and a surfactant; (ii) there is a high concentration of surfactant relative to oil; (iii) the system is optically clear; (iv) the phases do not separate by centrifugation; and (v) the system forms spontaneously.

Thus, for purposes of this invention, an emulsion is considered as containing structures having an average diameter of more than 100 nanometer (0.1 micron/1,000 angstrom Å), whereas a microemulsion contains structures having an average diameter of less than 100 nanometer (0.1 micron/1,000 angstrom Å), preferably less than 50 nanometer (0.05 micron/500 angstrom Å). Clarity or transparency is controlled to a great extent by the structure size of the dispersed phase. The scattering of light is dependent on the structure size. Therefore, clear or transparent compositions according to this invention are a single phase without droplets or structures when viewed with the naked eye, as defined hereafter.

In addition, emulsions are recognized as inherently unstable systems separating with time. In contrast, microemulsions according to this invention form spontaneously and are stable indefinitely. The order of addition of the components does not influence their formation, and simple hand shaking in the temperature range of their stability is sufficient to cause the one phase microemulsions to form.

These spontaneously formed single phase clear microemulsions have particular value in the personal care arena. Because of the unique volatility characteristics of the cyclic methyl siloxane component of the ternary system, it can be used alone, or blended with other cosmetic fluids, to form a variety of over-the-counter personal care products.

Thus, it is useful as a carrier in antiperspirants and deodorants, since it leaves a dry feel, and does not cool the skin upon evaporation. It is lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance gloss and drying time, and provide conditioning benefits. In cosmetics, it will function as a leveling and spreading agent for pigments in make-ups, color cosmetics, foundations, blushes, lipsticks, eyeliners, mascaras, oil removers, color cosmetic removers, and powders. It is useful as a delivery system for oil and water soluble substances such as vitamins. When incorporated into sticks, gels, lotions, aerosols, and roll-ons, the ternary composition imparts a dry, silky-smooth, payout.

In addition, because these spontaneously formed clear one phase microemulsions exhibit a variety of advantageous and beneficial properties such as (i) clarity, (ii) very small structure size, (iii) ultra-low interfacial tensions, (iv) the ability to combine properties of water and oil in a single homogeneous fluid, (v) shelf stability, and (vi) ease of preparation; they have wide application in other arenas as well such as textile finishing.

BRIEF SUMMARY OF THE INVENTION

It is an object of the invention to form a single phase clear microemulsion by simply combining (i) water; (ii) a cyclic or short chain linear methyl siloxane; and (iii) a nonionic surfactant or a combination of a nonionic surfactant and a cationic surfactant.

This is significant, because clear products can be made without involving the use of high shear, heretofore required to obtain the small structure size necessary to achieve clarity.

These single phase clear microemulsions form spontaneously in the sense that they do not require energy input by means of mixing and shear devices. Thus, a turbine, impeller, colloid mill, homogenizer, or sonicator, is not required to form these systems. It is only necessary that the appropriate amounts of the three components be added to a suitable container, and the container hand shaken. Of course, the components can be mixed or sheared with more energy input, and the clear single phase system will still be obtained, but no advantage results from such additional energy usage.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

This invention relates to the use of certain surfactants or mixtures of surfactants to create thermodynamically stable optically transparent microemulsions of silicone oils. The preferred surfactant is an ethoxylated alcohol surfactant, optionally combined with a cationic single or double tailed quaternary ammonium salt surfactant. The total concentration of the surfactant required to form these single phase systems is low, and the surfactant or surfactant mixture can be tailored to control the temperature window of a suitable microemulsion phase.

The unique and novel feature of the invention is its ability to prepare spontaneously, microemulsions of silicone oils using small amounts of a surfactant or surfactant mixture, as well as its ability to control a temperature range by the judicious selection of components of ternary systems for the provision of a range of stable compositions.

It is believed that this is the first practical demonstration of an efficient method for preparing microemulsions of silicone oils using such surfactants. Conventional wisdom has revealed that large amounts of ethoxylated alcohol surfactants are needed to form such one phase stable mixtures. According to one embodiment of this invention, however, the addition of a quaternary ammonium surfactant can reduce the overall amount of surfactant necessary to form such microemulsions by a factor of four on a weight percent basis, and thereby provide a more viable approach for commercial purposes.

As noted previously, these microemulsions are useful in many personal care applications, but especially as a deodorant or skin care lotion, and they can be used for delivering lipid soluble perfumes. In addition, the microemulsions can be used as a source of very small, i.e., below 50 nm, droplets of silicone oil for use in textile finishing and as an additive in a conditioning shampoo. They also provide an alternative to the more volatile solvents typically used for dilution of silicone oils; and because they exist as a single phase, the microemulsions have been found to be much easier to process.

Compositions according to this invention are stable within a certain temperature window, i.e., about 15–75° C., which depends upon the surfactant or surfactant mixture utilized in their preparation. This window of stability can be varied by a careful selection of surfactant(s) in order to provide a temperature range of particular interest. All compositions, however, become unstable at temperatures below about zero ° C.

Microemulsions according to the invention are thermodynamically stable, ternary, isotropic mixtures of water (A), a silicone oil (B), and one or more surfactants (C). More particularly, the microemulsions are compositions which exist in the single phase of a ternary diagram for such systems.

Thus, a typical temperature-composition phase diagram for a ternary mixture of water (A), silicone oil (B), and nonionic surfactant(s) (C), has temperature expressed in degrees Centigrade as the y-axis variable, and it has the weight percent of the surfactant expressed as gamma for the x-axis variable.

These types of diagram generally show a composition where alpha is defined as the weight of oil divided by the weight of oil plus water, as a percentage. Therefore, equal amounts of oil and water will be alpha equal 50. Other diagram exist for alpha varying from 50. Such diagram can be extracted from the phase prism diagram of each ternary system that maps the progression of the phase behavior of the ternary system as a function of temperature and composition.

A temperature-composition phase diagram can be divided into at least four regions. There exists a one-phase region, a three-phase region, and a pair of two-phase regions.

In the one-phase region, which is the region of interest according to this present invention, the surfactant (C) solubilizes all of the oil (B) and water (A) into a single equilibrium microemulsion phase. The lowest amount of surfactant (C) necessary to achieve this solubilization occurs at a surfactant concentration $\gamma_{min}$. Gamma is defined as $\gamma = C/A+B+C$. In this relationship, $\gamma_{min}$ represents the efficiency of a particular surfactant (C).

The ternary composition according to this invention contains (i) water, (ii) a cyclic or short chain linear methyl siloxane, and (iii) a nonionic surfactant or a combination of a nonionic surfactant and cationic surfactant. The three components can be combined to form clear one phase compositions without the addition of other materials.

Thus, the composition can be prepared with or without the inclusion of such non-essential ingredients as salts; co-surfactants; monohydroxy alcohols; and diols and triols such as ethylene glycol and glycerol. The ability to eliminate such non-essential ingredients is especially beneficial and advantageous, as it obviates the need for refractive index matching, often resorted to in the past to achieve clear or transparent products.

The three components can be combined in any given order of addition. While heat enhances solubility, lowers surface tension, and reduces viscosity, its application is not required. Room temperature (20–25°C./68–77° F.) is sufficient in most cases.

The oil component of the ternary composition is a cyclic methyl siloxane having the formula $\{(CH_3)_2SiO\}_x$ in which x is 3–6, or a short chain linear methyl siloxanes having the formula $(CH_3)_3SiO\{(CH_3)_2SiO\}_ySi(CH_3)_3$ in which y is 0–5.

Some suitable cyclic methyl siloxanes are hexamethylcyclotrisiloxane ($D_3$), a solid with a boiling point of 134° C. and the formula $\{(Me_2)SiO\}_3$; octamethylcyclotetrasiloxane ($D_4$) with a boiling point of 176° C., a viscosity of 2.3 mm²/s, and the formula $\{(Me_2)SiO\}_4$; decamethylcyclopentasiloxane ($D_5$) with a boiling point of 210° C., a viscosity of 3.87 mm²/s, and the formula $\{(Me_2)SiO\}_5$; and dodecamethylcyclohexasiloxane ($D_6$) with a boiling point of 245° C., a viscosity of 6.62 mm²/s and the formula $\{(Me_2)SiO\}_6$.

Some suitable short chain linear methyl siloxanes are hexamethyldisiloxane (MM) with a boiling point of 100° C., viscosity of 0–65 mm²/s, and formula $Me_3SiOSiMe_3$; octamethyltrisiloxane (MDM) with a boiling point of 152° C., viscosity of 1.04 mm²/s, and formula $Me_3SiOMe_2SiOSiMe_3$; decamethyltetrasiloxane ($MD_2M$) with a boiling point of 194° C., viscosity of 1.53 mm²/s, and formula $Me_3SiO(Me_2SiO)_2SiMe_3$; dodecamethylpentasiloxane ($MD_3M$) with a boiling point of 229° C., viscosity of 2.06 mm²/s, and formula $Me_3SiO(Me_2SiO)_3SiMe_3$; tetradecamethylhexasiloxane ($MD_4M$) with a boiling point of 245° C., viscosity of 2.63 mm²/s, and formula $Me_3SiO(Me_2SiO)_4SiMe_3$; and hexadecamethylheptasiloxane ($MD_5M$) with a boiling point of 270° C., viscosity of 3.24 mm²/s, and formula $Me_3SiO(Me_2SiO)_5SiMe_3$.

As noted above, the composition contains a nonionic surfactant. The nonionic surfactant should be a non-silicon atom containing nonionic emulsifier. Most preferred for this invention are alcohol ethoxylates $R—(OCH_2CH_2)_aOH$, more particularly fatty alcohol ethoxylates. Such fatty alcohol ethoxylates contain in their molecule the characteristic group $—(OCH_2CH_2)_aOH$, which is attached to a fatty hydrocarbon residue R of about eight to twenty carbon atoms, such as lauryl ($C_{12}$), cetyl ($C_{16}$) and stearyl ($C_{18}$). While "a" can have a value of from one to about one hundred, it is typically about 12 to about 40.

Some examples of suitable nonionic surfactants for use according to the invention are polyoxyethylene (4) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether.

These and other such fatty alcohol ethoxylates are readily available commercially under various names such as ALFONIC®, BRIJ, GENAPOL®, NEODOL®, SURFONIC®, and TRYCOL.

The composition may also contains a cationic surfactant in addition to the nonionic surfactant. Cationic surfactants useful in the invention include compounds containing quaternary ammonium hydrophilic moieties in the molecule which are positively charged such as the quaternary ammonium salts $R'R"R'"R""N^+X^-$. Most preferred are the dialkyldimethylammonium salts $R'R"N^+(CH_3)_2X^-$, where R', R", R"', and R"" represent alkyl groups typically containing 12–30 carbon atoms, or alkyl groups derived from tallow, coconut oil, or soy, for example; and X represents halogen such as chlorine or bromine.

Representative quaternary ammonium salts which may be employed are didodecyldimethylammonium bromide (DDAB), dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide (DTAB).

These and other such quaternary ammonium salts are readily available commercially under various names such as ADOGEN, ARQUAD, TOMAH, and VARIQUAT.

Compositions according to the invention contain 40–95% by weight of the cyclic or short chain linear methyl siloxane and water. The cyclic or short chain linear methyl siloxane and water are present in the single phase composition in a ratio of 1–60 percent by weight of cyclic or short chain linear methyl siloxane and 40–99 percent by weight of water.

The composition also contains 5–60% by weight of a surfactant. The surfactant may comprise only a nonionic surfactant, or in an alternate embodiment of the invention, the surfactant may comprise a combination of a nonionic surfactant and a cationic surfactant. In either embodiment, the cationic surfactant and the nonionic surfactant are present in the single phase composition in a ratio of 0–40 percent by weight of the cationic surfactant and 60–100 percent by weight of the nonionic surfactant. Most preferred, however, is a ratio of 1–40 percent by weight of a cationic surfactant and 60–99 percent by weight of a nonionic surfactant.

The cyclic or short chain linear methyl siloxane in the single phase composition most preferably should have an average structure or droplet diameter of less than about 50 nanometer in order to provide clarity. The criteria used to determine optical clarity is whether text can be read with the naked eye through a two centimeter diameter bottle filled with the one phase microemulsion.

For example, as noted in the textbook *Microemulsions Theory and Practice,* Edited by Leon M. Prince, Academic Press, Inc., Pages 7–10, New York (1977), "Visual recognition of microemulsions should not be taken lightly. In fact, the microemulsion chemist should train himself carefully in this art. Use of sunlight rather than an artificial source of light is recommended. The eye is better than a microscope because the limit of resolution of a light microscope in blue light is only about 0.1 μm so that droplets smaller than 0.14 μm cannot be seen".

EXAMPLES

The following examples illustrate the invention in more detail.

Example 1

An optically clear single phase composition was formed spontaneously at temperatures ranging from 43–50° C. by merely adding to a container 50 parts of deionized water, 50 parts of octamethylcyclotetrasiloxane, and 92.3 parts of ethoxylated alcohol surfactant $R—(OCH_2CH_2)_aOH$ where R was $C_8H_{17}$ and a was 3. The mixture was gently stirred.

Example 2

An optically clear single phase composition was formed spontaneously at temperatures ranging from 51–61° C. by merely adding to a container 50 parts of deionized water, 50 parts of decamethylcyclopentasiloxane, and 127.3 parts of ethoxylated alcohol surfactant $R—(OCH_2CH_2)_aOH$ where R was $C_8H_{17}$ and a was 3. The mixture was gently stirred.

Example 3

An optically clear single phase composition was formed spontaneously at temperatures ranging from 55–66° C. by merely adding to a container 50 parts of deionized water, 50 parts of decamethyltetrasiloxane, and 150 parts of ethoxylated alcohol surfactant R—(OCH$_2$CH$_2$)$_a$OH where R was C$_8$H$_{17}$ and a was 3. The mixture was gently stirred.

Example 4

An optically clear single phase composition was formed spontaneously at temperatures ranging from 69–73° C. by merely adding to a container 50 parts of deionized water, 50 parts of octamethylcyclotetrasiloxane, and 66.7 parts of ethoxylated alcohol surfactant R—(OCH$_2$CH$_2$)$_a$OH where R was C$_{12}$H$_{25}$ and a was 5. The mixture was gently stirred.

Example 5

An optically clear single phase composition was formed spontaneously at temperatures ranging from about 15–35° C. by merely adding to a container 50 parts of deionized water, 50 parts of octamethylcyclotetrasiloxane, and 51 parts of ethoxylated alcohol surfactant R—(OCH$_2$CH$_2$)$_a$OH where R was C$_{12}$H$_{25}$ and a was 3. The mixture was gently stirred.

Example 6

An optically clear single phase composition was formed spontaneously at temperatures ranging from 66–73° C. by merely adding to a container 50 parts of deionized water, 50 parts of octamethylcyclotetrasiloxane, 15.9 parts of ethoxylated alcohol surfactant R—(OCH$_2$CH$_2$)$_a$OH where R was C$_8$H$_{17}$ and a was 3, and 1.7 parts of quaternary ammonium salt cationic surfactant didodecyldimethylammonium bromide. The mixture was gently stirred.

Example 7

An optically clear single phase composition was formed spontaneously at temperatures ranging from 48–70° C. by merely adding to a container 50 parts of deionized water, 50 parts of octamethylcyclotetrasiloxane, 18 parts of ethoxylated alcohol surfactant R—(OCH$_2$CH$_2$)$_a$OH where R was C$_{12}$H$_{25}$ and a was 3, and 4 parts of quaternary ammonium salt cationic surfactant didodecyldimethylammonium bromide. The mixture was gently stirred.

Example 8

An optically clear single phase composition was formed spontaneously at temperatures ranging from 61–66° C. by merely adding to a container 50 parts of deionized water, 50 parts of decamethyltetrasiloxane, 30.8 parts of ethoxylated alcohol surfactant R—(OCH$_2$CH$_2$)$_a$OH where R was C$_{12}$H$_{25}$ and a was 3, and 4.3 parts of quaternary ammonium salt cationic surfactant didodecyldimethylammonium bromide. The mixture was gently stirred.

Example 9

An optically clear single phase composition was formed spontaneously at temperatures ranging from 35–43° C. by merely adding to a container 90 parts of a five percent solution of sodium chloride in water, 10 parts of octamethylcyclotetrasiloxane, and 17.6 parts of ethoxylated alcohol surfactant R—(OCH$_2$CH$_2$)$_a$OH where R was C$_{12}$H$_{25}$ and a was 5. The mixture was gently stirred.

Example 10

An optically clear single phase composition was formed spontaneously at temperatures ranging from 63–71° C. by merely adding to a container 95 parts of a one percent solution of sodium chloride in water, 5 parts of octamethylcyclotetrasiloxane, 10 parts of ethoxylated alcohol surfactant R—(OCH$_2$CH$_2$)$_a$OH where R was C$_{12}$H$_{25}$ and a was 5, and 1.1 parts of quaternary ammonium salt cationic surfactant didodecyldimethylammonium bromide. The mixture was gently stirred.

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A microemulsion comprising at 15–75° C. a single phase composition containing (i) 40–95% by weight of a short chain linear methyl siloxane and water, the short chain linear methyl siloxane having the formula (CH$_3$)$_3$SiO{(CH$_3$)$_2$SiO}$_y$Si(CH$_3$)$_3$ in which y is 0–5, the short chain linear methyl siloxane and water being present in the single phase composition in a ratio of 1–60 percent by weight of short chain linear methyl siloxane and 40–99 percent by weight of water; and (ii) 5–60% by weight of one or more surfactants, the surfactants being a cationic surfactant and a nonionic surfactant present in the single phase composition in a ratio of 0–40 percent by weight of the cationic surfactant and 60–100 percent by weight of the nonionic surfactant; the short chain linear methyl siloxane being present in the single phase composition as droplets having an average diameter of less than about 50 nanometer.

2. A microemulsion according to claim 1 in which the short chain linear methyl siloxane is selected from the group consisting of hexamethyldisiloxane, octamethyltrisiloxane, decamethyltetrasiloxane, dodecamethylpentasiloxane, tetradecamethylhexasiloxane, and hexadecamethylheptasiloxane.

* * * * *